United States Patent
Zheng et al.

(10) Patent No.: US 9,295,962 B2
(45) Date of Patent: Mar. 29, 2016

(54) PRODUCTION OF PARA-XYLENE

(75) Inventors: Xiaobo Zheng, Houston, TX (US);
Mark P. Hagemeister, Houston, TX (US); Timothy P. Bender, Houston, TX (US); Robert G. Tinger, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 13/487,651

(22) Filed: Jun. 4, 2012

(65) Prior Publication Data
US 2012/0316375 A1 Dec. 13, 2012

Related U.S. Application Data

(60) Provisional application No. 61/495,530, filed on Jun. 10, 2011.

(51) Int. Cl.
*C07C 15/067* (2006.01)
*C07C 7/12* (2006.01)
*B01J 8/18* (2006.01)
(Continued)

(52) U.S. Cl.
CPC ............... *B01J 8/18* (2013.01); *B01J 8/1827* (2013.01); *C07C 2/864* (2013.01); *C07C 5/2729* (2013.01); *C07C 7/12* (2013.01); *C07C 7/14* (2013.01); *C07C 7/1485* (2013.01);
(Continued)

(58) Field of Classification Search
CPC .......... C07C 15/067; C07C 7/00; C07C 7/12; C07C 7/13; C07C 37/006; C07C 37/11; C07C 39/04; C07C 39/07

USPC ......... 585/446, 450, 451, 802, 804, 805, 820, 585/833, 853, 854
See application file for complete search history.

(56) References Cited

U.S. PATENT DOCUMENTS

| 3,969,422 A | 7/1976 | Neuzil et al. |
| 5,338,453 A * | 8/1994 | Fraini et al. .................. 210/634 |

(Continued)

FOREIGN PATENT DOCUMENTS

| JP | 10-298117 | 11/1998 |
| WO | WO 00/69796 | 11/2000 |

(Continued)

OTHER PUBLICATIONS

Higson, S. Acid and Base Interactions. Standard Wet Chemical and Reagent-Based Techniques. Chapter 3. Analytical Chemistry. 2004. pp. 67-69 http://www.knovel.com/web/portal/knovel_content?p_p_id=EXT_KNOVEL_CONTENT&p_p_action=1&p_p_state=normal&p_p_mode=view&p_p_col_id=column-1&p_p_col_count=1&_EXT_KNOVEL_CONTENT_struts_action=/ext/knovel_content/.*

(Continued)

*Primary Examiner* — Walter D Griffin
*Assistant Examiner* — Jelitza Perez

(57) ABSTRACT

The invention is a process for producing paraxylene, benzene and/or toluene is alkylated with methanol in the presence of a catalyst under conditions effective to convert said benzene and/or toluene to xylene and produce a product stream containing water, xylene and one or more phenolic impurities. The said product stream is separated into a water-rich stream and a xylene-rich stream containing one or more phenolic impurities and at least a portion of the xylene-rich stream is contacted with an aqueous solution of a base under conditions to remove at least some of the phenolic impurities from the xylene-rich stream portion.

10 Claims, 8 Drawing Sheets

(51) Int. Cl.
*C07C 2/86* (2006.01)
*C07C 5/27* (2006.01)
*C07C 7/14* (2006.01)
*C07C 7/148* (2006.01)

(52) U.S. Cl.
CPC ... *B01J 2219/00006* (2013.01); *C07C 2523/04* (2013.01); *C07C 2529/40* (2013.01); *C07C 2529/65* (2013.01)

(56) References Cited

U.S. PATENT DOCUMENTS

| | | | |
|---|---|---|---|
| 5,997,731 A | 12/1999 | Suarez | |
| 6,284,695 B1 | 9/2001 | Winter | |
| 6,423,879 B1 | 7/2002 | Brown et al. | |
| 6,504,072 B1 | 1/2003 | Brown et al. | |
| 6,642,426 B1* | 11/2003 | Johnson et al. | 585/449 |
| 2009/0134094 A1* | 5/2009 | Falkiner et al. | 210/708 |
| 2010/0261941 A1* | 10/2010 | Hagemeister et al. | 585/470 |
| 2010/0305378 A1* | 12/2010 | Galloway et al. | 585/449 |

FOREIGN PATENT DOCUMENTS

| | | |
|---|---|---|
| WO | WO 2004/000974 | 12/2003 |
| WO | WO 2009/080342 | 7/2009 |
| WO | WO 2009080342 A1 * | 7/2009 |
| WO | WO 2010/120616 | 10/2010 |

OTHER PUBLICATIONS

Cramer, Stephen D.; Covino, Bernard S., Jr. (2006). ASM Handbook, vol. 13C—Corrosion: Environments and Industries. (pp: p. 978). ASM International. Online version available at: http://www.knovel.com/web/portal/browse/display?_EXT_KNOVEL_DISPLAY_bookid=3130&VerticalID=0.*

Busca et al., "*Technologies for the removal of phenol from fluid streams: A short review of recent developments*", Journal of Hazardous Materials, 160, pp. 265-288 (2008).

Palma et al., "*Batch phenol removal from methyl isobutyl ketone by liquid-liquid extraction with chemical reaction*", Chemical Engineering and Processing, vol. 46, Issue 8, pp. 764-768 (2007).

Yashima et al., "*Alkylation on Synthetic Zeolites*", Journal of Catalysis, vol. 16, pp. 273-280 (1970).

Gentry et al., "Innovative Technology", International Journal of Hydrocarbon Engineering, Palladian Publications, Elstead, GB, vol. 7, No. 6, Jun. 2002, pp. 49-51.

* cited by examiner

PRODUCTION OF PARA-XYLENE

PRIORITY CLAIM

This application claims the benefit of Provisional Application No. 61/495,530, filed Jun. 10, 2011, the disclosure of which is incorporated by reference in its entirety.

FIELD

This invention relates to a process for producing paraxylene by the alkylation of benzene and/or toluene with methanol.

BACKGROUND

Of the xylene isomers, paraxylene is of particularly high value since it is useful in the manufacture of terephthalic acid which is an intermediate in the manufacture of synthetic fibers. Equilibrium mixtures of xylene isomers either alone or in further admixture with ethylbenzene, such as obtained by catalytic reforming of naphtha, generally contain only about 22-24 wt % paraxylene. Separation of paraxylene from such mixtures typically requires superfractionation and multistage refrigeration steps, energy intensive adsorption processes and the like. There is therefore a continuing need to provide processes for producing xylenes which are highly selective for para-isomer.

One known method for producing xylenes involves the alkylation of toluene with methanol over a solid acid catalyst, such as described by Yashima et al. in the Journal of Catalysis 16, 273-280 (1970). These workers reported selective production of paraxylene over the approximate temperature range of 200 to 275° C., with the maximum yield of paraxylene in the mixture of xylenes, i.e., about 50% of the xylene product mixture, being observed at 225° C. Higher temperatures were reported to result in an increase in the yield of meta-xylene and a decrease in production of para and ortho-xylenes.

More recently, selectivities to paraxylene in excess of 90 wt % (based on total $C_8$ aromatic product) have been reported by reacting toluene with methanol in the presence of a catalyst comprising a porous crystalline material, preferably a medium-pore zeolite and particularly ZSM-5, having a Diffusion Parameter for 2,2-dimethylbutane of about 0.1-15 $sec^{-1}$ when measured at a temperature of 120° C. and a 2,2 dimethylbutane pressure of 60 torr (8 kPa). See U.S. Pat. Nos. 6,423,879 and 6,504,072.

However, irrespective of the selectivity to paraxylene, the alkylation of benzene and/or toluene with methanol inevitably results in the production of a variety of oxygenate by-products as a result of side reactions of methanol with itself and the various aromatic species present. Such oxygenate by-products include water, alcohols, ethers, ketones, aldehydes, acid and phenolic impurities and, depending on their boiling point, are either returned to the alkylation reactor in recycle streams or leave the process through one or more product streams. In particular, the paraxylene-rich product stream tends to contain phenolic impurities such as phenol, methyl phenols and dimethyl phenols. As a result, when the paraxylene is recovered from this product stream, generally by crystallization or by adsorption, the paraxylene product and/or the residual paraxylene-depleted xylene fraction typically contains from one to several hundred ppmw of phenolic impurities. (As used herein, ppmw means parts per million, by weight, relative to the entire weight of whatever stream is referred to). These impurities limit the value of the paraxylene-depleted xylene fraction and generally mean that the fraction can only be used as a blending stream for automotive gasoline. Additionally in the case where phenolic impurities contaminate the paraxylene product fraction there is a potential for downstream processes to be impacted resulting in a decreased downstream performance of the paraxylene purification step(s).

According to the present invention, it has now been found that the concentration of phenolic impurities in a xylene stream produced by alkylation of benzene and/or toluene with methanol can be reduced to trace levels, such as below 0.1 ppmw, by one or more washing treatments with an aqueous solution of a base (caustic). The resultant treated xylene stream, if necessary after water washing to remove any phenate-containing solution (solution containing phenolate or phenylate; the salt of a metal containing the phenoxy radical) and ensuring all trace aqueous base solution, trace metals (for example sodium or potassium ions), and water is removed, can, in embodiments, then be recycled to the other xylene processing units and generate additional paraxylene or the treated xylene stream can be used to manufacture other higher value xylene products such as but not limited to paraxylene. In embodiments, a contaminant-free mixed-xylene by-product may be produced and/or sold for further processing or used as a solvent.

SUMMARY

The invention resides in a process for producing paraxylene, the process comprising:

(a) alkylating benzene and/or toluene with methanol in the presence of a catalyst under conditions effective to convert said benzene and/or toluene to xylene and produce a product stream containing water, xylene and one or more phenolic impurities;

(b) separating said product stream into a water-rich stream and a xylene-rich stream containing one or more phenolic impurities; and (c) contacting at least a portion of said xylene-rich stream with an aqueous solution of a base under conditions to remove at least a portion of said phenolic impurities from said xylene-rich stream portion.

Conveniently, the phenolic impurities are selected from phenol, methyl phenol and dimethyl phenol.

In an embodiment, the contacting with an aqueous solution of a base under conditions to remove at least a portion of said phenolic impurities reduces said the total level of phenolic impurities by at least 90 wt %, preferably at least 95 wt %, still more preferably at least 99.0 wt %, yet still more preferably at least 99.90 wt %, relative to the level of total phenolic impurities in the stream contacted.

In another embodiment, the xylene-rich stream portion contacted with said aqueous solution of a base in (c) comprises from about 0.2 ppmw to about 1000 ppmw of phenol and the contacting (c) reduces the level of phenol in said xylene-rich stream portion to less than 0.1 ppmw. In other embodiments, the xylene-rich stream portion contacted with said aqueous solution of a base in (c) comprises from about 20 ppmw to about 1000 ppmw of phenol and the contacting (c) reduces the level of phenol in said xylene-rich stream portion to less than 10 ppmw, preferably less than 1.0 ppmw, still more preferably less than 0.1 ppmw. In still other embodiments, said contacting in step (c) reduces the level of phenol by at least 90 wt %, preferably at least 95 wt %, still more preferably at least 99.0 wt %, yet still more preferably at least 99.90 wt %, relative to the level of phenol in said xylene-rich stream.

In a further embodiment, the xylene-rich stream contacted with said aqueous solution of a base in (c) comprises from about 0.2 ppmw to about 1000 ppmw of methyl phenol and the contacting (c) reduces the level of methyl phenol in said xylene-rich stream portion to less than 0.1 ppmw. In other embodiment, the xylene-rich stream contacted with said aqueous solution of a base in (c) comprises from about 20 ppmw to about 1000 ppmw of methyl phenols and the contacting (c) reduces the level of methyl phenol in said xylene-rich stream portion to less than 10 ppmw, preferably 0.1 ppmw. In still other embodiments, said contacting in step (c) reduces the level of methyl phenol by at least 90 wt %, preferably at least 95 wt %, still more preferably at least 99.0 wt %, yet still more preferably at least 99.90 wt %, relative to the level of methyl phenol in said xylene-rich stream.

In yet a further embodiment, the xylene-rich stream contacted with said aqueous solution of a base in (c) comprises from about 0.5 ppmw to about 1000 ppmw of dimethyl phenol and the contacting (c) reduces the level of dimethyl phenols in said xylene-rich stream portion to less than 0.1 ppmw. In other embodiments, the xylene-rich stream contacted with said aqueous solution of a base in (c) comprises from about 20 ppmw to about 1000 ppmw of dimethyl phenol and the contacting (c) reduces the level of dimethyl phenol in said xylene-rich stream portion to less than 10 ppmw, preferably 0.1 ppmw. In still other embodiments, said contacting in step (c) reduces the level of di-methyl phenol by at least 90 wt %, preferably at least 95 wt %, still more preferably at least 99.0 wt %, yet still more preferably at least 99.90 wt %, relative to the level of di-methyl phenol in said xylene-rich stream.

Conveniently, the process further comprises:

(d) recovering paraxylene from the xylene-rich stream separated in (b) to leave a paraxylene-depleted stream; and (e) feeding said paraxylene-depleted stream to said contacting (c).

In additional embodiments, when the caustic wash is employed upstream of a paraxylene adsorption process (such as Parex™ or Eluxyl™ process) it is highly advantageous to remove all traces of caustic, including both the basic species and metal ions potentially present as these could impact the adsorbents utilized by displacing the metals in the zeolite structure, such as potassium. It is also important to remove water down to acceptably low levels.

In embodiments, aqueous base contacting can be before or after paraxylene separation, such as shown in FIG. 5 discussed hereinbelow.

In the above embodiments, the base is advantageously an alkali metal compound, such as sodium hydroxide. Typically, the aqueous solution comprises a 0.01 N to 10 N sodium hydroxide solution.

Conveniently, the contacting (c) is conducted for a time from about 0.5 to about 60 minutes. It can be liquid-liquid or liquid-vapor contacting (with the caustic wash in the liquid phase in both embodiments; the xylene fraction can be in the liquid or vapor phase, or both).

In embodiments, the contacting (c) is conducted in a wash tower.

Conveniently, the base reacts with the phenolic impurities during said contacting (c) to produce a phenate salt which dissolves in said aqueous solution to produce an aqueous phase containing said phenate salt and an organic phase depleted in said phenolic impurities and the process further comprises:

(f) separating said organic phase from said aqueous phase.

In one embodiment, the process further comprises:

(g) washing said organic phase with water to remove any phenate-containing aqueous phase entrained or dissolved therein and to remove any residual trace aqueous base. In an embodiment the resulting organic phase after removal of any phenate-containing aqueous phase may be sent to an additional step to remove trace aqueous base, metal ions, and residual water (by one or more stages of water washing, ion exchange resin, adsorptive removal, or pasteurization). In another embodiment the caustic wash, phenate removal, trace aqueous base and water removal steps could be combined to increase cost effectiveness. This may be accomplished by use of resins. Examples of suitable resins are commercially available from companies such as Rohm and Haas or Sigma Aldrich. In an advantageous embodiment water removal may be accomplished by pasteurization by fractionation or adsorbent driers.

Conveniently, said aqueous phase separated in (f) has a pH greater than 7 and is combined with said water-rich stream separated in (b) to neutralize acidic impurities in said water-rich stream.

DETAILED DESCRIPTION OF THE EMBODIMENTS

Figure 1:
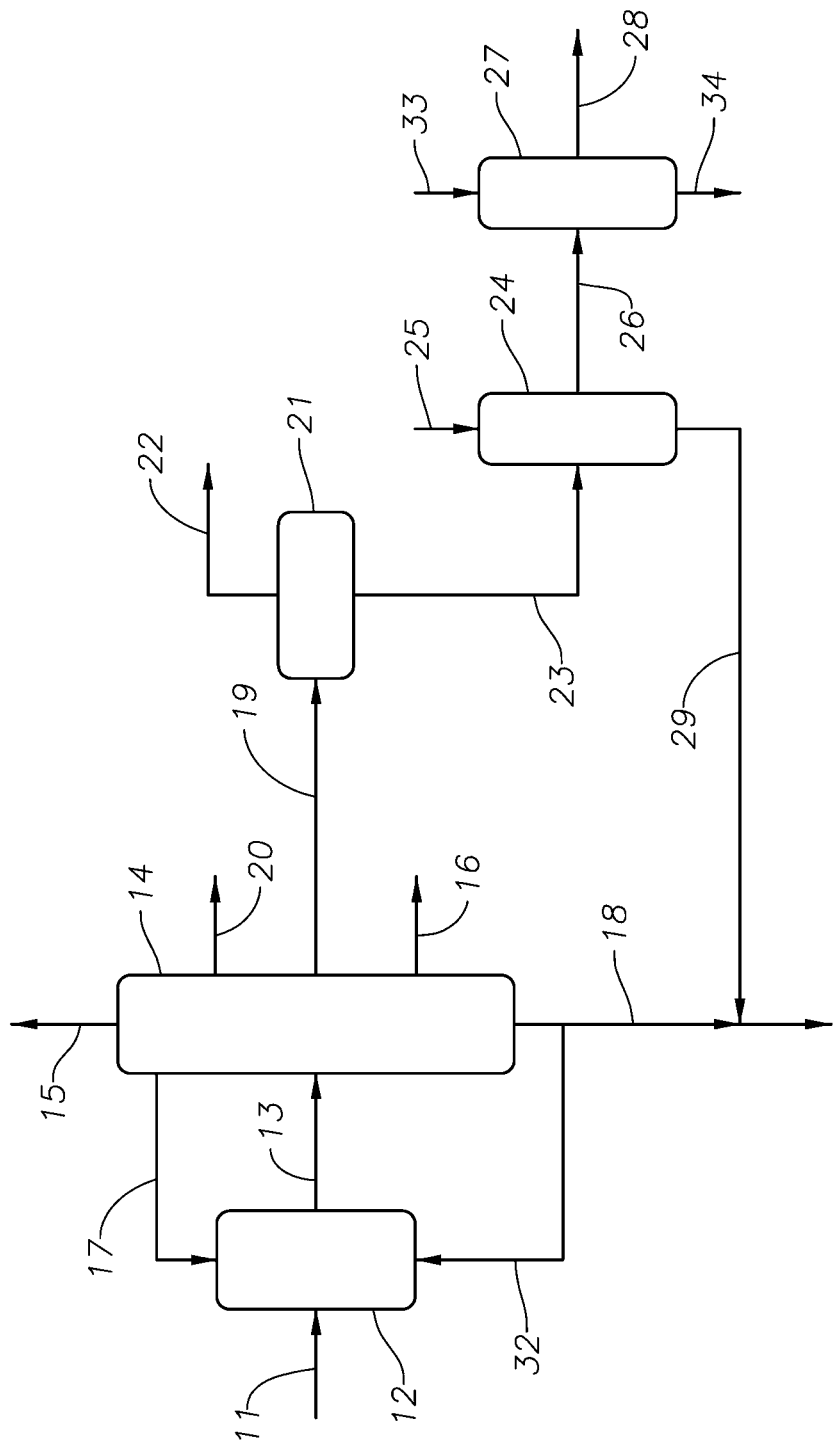
FIGS. 1 through 5 are schematic illustrations of embodiments of the present invention showing non-limiting examples of a process for producing paraxylene by alkylating benzene and/or toluene with methanol and including caustic wash downstream of said alkylating. In these FIGS. 1-5, like reference numerals are used to denote like parts throughout the several views.

Described herein is a process for producing paraxylene by the catalytic alkylation of benzene and/or toluene with methanol. The alkylation process produces a paraxylene-rich mixture of xylene isomers, together with water and some phenolic impurities. The present process provides an improved method of separating and purifying the alkylation effluent in a way which maximizes the recovery of the xylene product and, in a preferred embodiment, simplifies treatment of the waste water stream.

Alkylation Process

The alkylation process employed herein can employ any aromatic feedstock comprising toluene and/or benzene, although in general it is preferred that the aromatic feed contains at least 90 wt %, especially at least 99 wt %, of benzene, toluene or a mixture thereof. An aromatic feed containing at least 99 wt % toluene is particularly desirable. Similarly, although the composition of the methanol-containing feed is not critical, it is generally desirable to employ feeds containing at least 90 wt %, especially at least 99 wt %, of methanol.

The catalyst employed in the alkylation process is generally a porous crystalline material and, in one preferred embodiment, is a porous crystalline material having a Diffusion Parameter for 2,2 dimethylbutane of about 0.1-15 sec$^{-1}$ when measured at a temperature of 120° C. and a 2,2 dimethylbutane pressure of 60 torr (8 kPa).

As used herein, the Diffusion Parameter of a particular porous crystalline material is defined as $D/r^2 \times 10^6$, wherein D is the diffusion coefficient (cm$^2$/sec) and r is the crystal radius (cm). The diffusion parameter can be derived from sorption measurements provided the assumption is made that the plane sheet model describes the diffusion process. Thus for a given sorbate loading Q, the value $Q/Q_{eq}$, where $Q_{eq}$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The porous crystalline material is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the present process.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one embodiment, the zeolite employed in the process of the invention is ZSM-5 having a silica to alumina molar ratio of at least 250, as measured prior to any treatment of the zeolite to adjust its diffusivity.

Zeolite ZSM-5 and the conventional preparation thereof are described in U.S. Pat. No. 3,702,886. Zeolite ZSM-11 and the conventional preparation thereof are described in U.S. Pat. No. 3,709,979. Zeolite ZSM-12 and the conventional preparation thereof are described in U.S. Pat. No. 3,832,449. Zeolite ZSM-23 and the conventional preparation thereof are described U.S. Pat. No. 4,076,842. Zeolite ZSM-35 and the conventional preparation thereof are described in U.S. Pat. No. 4,016,245. ZSM-48 and the conventional preparation thereof is taught by U.S. Pat. No. 4,375,573. The entire disclosures of these U.S. patents are incorporated herein by reference.

The medium pore zeolites described above are preferred for the present process since the size and shape of their pores favor the production of p-xylene over the other xylene isomers. However, conventional forms of these zeolites have Diffusion Parameter values in excess of the 0.1-15 sec$^{-1}$ range desired for the present process. Nevertheless, the required diffusivity can be achieved by severely steaming the zeolite so as to effect a controlled reduction in the micropore volume of the catalyst to not less than 50%, and preferably 50-90%, of that of the unsteamed catalyst. Reduction in micropore volume is monitored by measuring the n-hexane adsorption capacity of the zeolite, before and after steaming, at 90° C. and 75 torr n-hexane pressure.

Steaming to achieve the desired reduction in the micropore volume of the porous crystalline material can be effected by heating the material in the presence of steam at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups IIA, IIIA, IIIB, IVA, VA, VB and VIA of the Periodic Table (IUPAC version). Conveniently, said at least one oxide modifier is selected from oxides of boron, magnesium, calcium, lanthanum and preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt %, such as between about 0.1 and about 10 wt %, based on the weight of the final catalyst.

Where the modifier includes phosphorus, incorporation of modifier in the alkylation catalyst is conveniently achieved by the methods described in U.S. Pat. Nos. 4,356,338, 5,110,776, 5,231,064 and 5,348,643, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %.

Representative phosphorus-containing compounds which may be used to incorporate a phosphorus oxide modifier into the catalyst of the invention include derivatives of groups represented by PX3, RPX2, R2PX, R3P, X3PO, (XO)3PO, (XO)3P, R3P=O, R3P=S, RPO2, RPS2, RP(O)(OX)$_2$, RP(S)(SX)2, R2P(O)OX, R2P(S)SX, RP(OX)2, RP(SX)2, ROP(OX)2, RSP(SX)2, (RS)2PSP(SR)2, and (RO)2POP(OR)2, where R is an alkyl or aryl, such as phenyl radical, and X is hydrogen, R, or halide. These compounds include primary, RPH2, secondary, R2PH, and tertiary, R3P, phosphines such as butyl phosphine, the tertiary phosphine oxides, R3PO, such as tributyl phosphine oxide, the tertiary phosphine sulfides, R3PS, the primary, RP(O)(OX)2, and secondary, R2P(O)OX, phosphonic acids such as benzene phosphonic acid, the corresponding sulfur derivatives such as RP(S)(SX)2 and R2P(S)SX, the esters of the phosphonic acids such as dialkyl phosphonate, (RO)2P(O)H, dialkyl alkyl phosphonates, (RO)2P(O)R, and alkyl dialkylphosphinates, (RO)P(O)R2; phosphinous acids, R2POX, such as diethylphosphinous acid, primary, (RO)P(OX)2, secondary, (RO)2POX, and tertiary, (RO)3P, phosphites, and esters thereof such as the monopropyl ester, alkyl dialkylphosphinites, (RO)PR2, and dialkyl alkyphosphinite, (RO)2PR, esters. Corresponding sulfur derivatives may also be employed including (RS)2P(S)H, (RS)2P(S)R, (RS)P(S)R2, R2PSX, (RS)P(SX)2, (RS)2PSX, (RS)3P, (RS)PR2, and (RS)2PR. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphoro-chloridites, $(RO)_2PCl$, dialkylphosphinochloroidites, $R_2PCl$, alkyl alkylphosphonochloridates, $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$, $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-$P_2O_5$ reaction products.

Representative boron-containing compounds which may be used to incorporate a boron oxide modifier into the catalyst of the invention include boric acid, trimethylborate, boron oxide, boron sulfide, boron hydride, butylboron dimethoxide, butylboric acid, dimethylboric anhydride, hexamethylborazine, phenyl boric acid, triethylborane, diborane and triphenyl boron.

Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium bromide, magnesium hydride, magnesium lactate, magnesium laurate, magnesium oleate, magnesium palmitate, magnesium salicylate, magnesium stearate and magnesium sulfide.

Representative calcium-containing compounds include calcium acetate, calcium acetylacetonate, calcium carbonate, calcium chloride, calcium methoxide, calcium naphthenate, calcium nitrate, calcium phosphate, calcium stearate and calcium sulfate.

Representative lanthanum-containing compounds include lanthanum acetate, lanthanum acetylacetonate, lanthanum carbonate, lanthanum chloride, lanthanum hydroxide, lanthanum nitrate, lanthanum phosphate and lanthanum sulfate.

The porous crystalline material employed in the process of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Ga. and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite.

The alkylation process can be conducted in any known reaction vessel but generally the methanol and aromatic feeds are contacted with the catalyst described above with the catalyst particles being disposed in one or more fluidized beds. Each of the methanol and aromatic feeds can be injected into the fluidized catalyst in a single stage. However, in one embodiment, the methanol feed is injected in stages into the fluidized catalyst at one or more locations downstream from the location of the injection of the aromatic reactant into the fluidized catalyst. For example, the aromatic feed can be injected into a lower portion of a single vertical fluidized bed of catalyst, with the methanol being injected into the bed at a plurality of vertically spaced intermediate portions of the bed and the product being removed from the top of the bed. Alternatively, the catalyst can be disposed in a plurality of vertically spaced catalyst beds, with the aromatic feed being injected into a lower portion of the first fluidized bed and part of the methanol being injected into an intermediate portion of the first bed and part of the methanol being injected into or between adjacent downstream catalyst beds.

The conditions employed in the alkylation stage of the present process are not narrowly constrained but, in the case of the methylation of toluene, generally include the following ranges: (a) temperature between about 500 and about 700° C., such as between about 500 and about 600° C.; (b) pressure of between about 1 atmosphere and about 1000 psig (between about 100 and about 7000 kPa), such as between about 10 psig and about 200 psig (between about 170 and about 1480 kPa); (c) moles toluene/moles methanol (in the reactor charge) of at least about 0.2, such as from about 0.2 to about 20; and (d) a weight hourly space velocity ("WHSV") for total hydrocarbon feed to the reactor(s) of about 0.2 to about 1000, such as about 0.5 to about 500 for the aromatic reactant, and about 0.01 to about 100 for the combined methanol reagent stage flows, based on total catalyst in the reactor(s).

Reference should also be made to systems and process disclosed in U.S. Provisional Patent Applications 61/512,271 and 61/506,309, which may be advantageously employed and/or integrated with the processes and apparatus disclosed herein.

Product Treatment and Recovery

The product of the reaction between the methanol and the aromatic feed is a gaseous effluent comprising paraxylene and other xylene isomers, water vapor, unreacted toluene and/or benzene, unreacted methanol, phenolic impurities, light olefins and other light gas by-products, and generally some $C_9$+ aromatic by-products. In addition, where the process is conducted in a fluidized catalyst bed, the effluent will contain some entrained solid catalyst and catalyst fines. Thus the gaseous effluent leaving the (final) fluidized bed reactor is generally passed through an integral cyclone separator to remove some of the entrained catalyst solids and return them to the alkylation reactor.

The product effluent leaves the alkylation reactor system at a high temperature, typically between about 500 and about 600° C. and initially may be passed through a heat exchanger so that the waste heat in the effluent stream may be recovered and used to heat other process stream(s). It is, however, preferred that any initial cooling of the product stream is limited so as to keep the effluent vapors well above the dew point, typically about 240° F. (116° C.).

Following further cooling, the effluent vapor stream is fed to a separation system, which may comprise one or more fractionation columns, where the unreacted methanol and aromatics are recovered and recycled to the alkylation step, the light and heavy hydrocarbons are removed and the remainder of effluent is separated into a liquid organic phase rich in xylene and a waste water stream. Part of the phenolic impurities is concentrated in the xylene-rich organic phase and part is dissolved in the waste water stream making the waste water stream acidic.

In one embodiment, after separation of the aqueous component, the xylene-rich organic phase is fed to one or more crystallizers where the paraxylene is selectively crystallized from the other xylene isomers leaving a para-depleted xylene filtrate containing the phenolic impurities. Typically, the phenolic impurities include phenol, methyl phenols and dimethyl phenols and are present in the xylene filtrate in an amount from about 0.2 ppmw to about 1000 ppmw of phenol, from about 0.2 ppmw to about 1000 ppmw of methyl phenols and from about 0.5 ppmw to about 1000 ppmw of dimethyl phenols.

The xylene filtrate is fed to a wash tower where the filtrate is contacted with an aqueous solution of a base, such as an alkali metal compound, particularly sodium hydroxide. Typically, the aqueous base solution comprises a 0.01 N to 10 N sodium hydroxide solution and the aqueous base solution is contacted with the xylene filtrate for about 0.5 to about 60 minutes. In the presence of the base, the phenolic impurities are removed from the xylene filtrate through the following reactions:

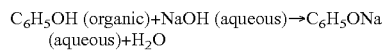

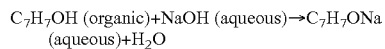

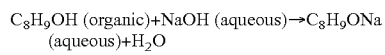

The reaction products, $C_6H_5ONa$, $C_7H_7ONa$ and $C_8H_9ONa$, are water soluble and stay with the spent caustic stream. The xylene filtrate stream remaining after the caustic wash is substantially free of phenolic impurities, containing less than 0.1 ppmw of each of phenol, methyl phenols and dimethyl phenols. If necessary, the castic wash may be repeated two, three or more times to reduce the level of phenolic impurities to the desired amount. In addition, a one or more final water washes may be employed to reduce the content of sodium phenate salts in any residual dissolved or entrained water in the xylene filtrate stream. The xylene filtrate stream may then be recycled via the separation system to the crystallizer(s) to generate more paraxylene or alternatively can be sold as xylene solvent.

If desired, the spent caustic stream from the caustic wash tower can be combined with the acidic waste water stream from the separation system to neutralize the waste water stream and thereby facilitate disposal of both aqueous streams.

Alternate embodiment after separation of the aqueous component, the xylene-rich organic phase containing the typical phenolic impurities that include phenol, methyl phenols and dimethyl phenols and are present in the xylene rich stream in an amount from about 0.2 ppmw to about 1000 ppmw of phenol, from about 0.2 ppmw to about 1000 ppmw of methyl phenols and from about 0.5 ppmw to about 1000 ppmw of dimethyl phenols.

The xylene rich stream from alkylation is fed to a wash tower where the filtrate is contacted with an aqueous solution of a base, such as an alkali metal compound, particularly sodium hydroxide. Typically, the aqueous base solution comprises a 0.01 N to 10 N sodium hydroxide solution and the aqueous base solution is contacted with the xylene filtrate for about 0.5 to about 60 minutes.

One embodiment of a process for producing paraxylene by the reaction of methanol with toluene will now be more particularly described with reference to FIG. 1, which illustrates the basic embodiment of a caustic wash downstream of one or more crystallizers 21, such as of a type per se well-known in the art, which are in turn downstream from the alkylation reactor 12, which may also be of a type per se well-known in the art. It will be appreciated by one of skill in the art that in this FIG. 1, as well as FIGS. 2-5 discussed further below, not all valves, condensers, heat exchangers, conduits, and the like, are shown, for convenience of view, but would be understood by one of ordinary skill in the art in possession of the present disclosure, and that such a system can be constructed by the same with no more than routine engineering skill. In this embodiment, a feed comprising methanol and toluene is supplied by line 11 (or they can be supplied separately and/or in multiple conduits) to an alkylation reactor 12, where the components of the feed react to produce a gaseous effluent 13 comprising xylene isomers, water vapor, unreacted toluene and methanol, phenolic impurities, and light and heavy by-products. The gaseous effluent is cooled by a heat exchanger (not shown) and is then fed by line 13 to a multi-stage separation system 14, shown as one unit for simplicity of view, where the light ($C_1$ to $C_4$) by-products are removed as overhead 15, $C_5$ and $C_6$ hydrocarbons are removed via line 20, the $C_9$+ heavies are removed as a bottoms stream 16, the unreacted toluene and methanol are recovered and recycled via line 17 to the reactor 12, an acidic waste water stream is removed via line 18 and a products stream containing xylenes and part of the phenolic impurities is recovered via line 19.

The products stream is fed by line 19 to one or more crystallizers 21 where paraxylene is crystallized from the product stream and recovered through line 22. The xylene filtrate remaining after removal of the crystalline paraxylene product contains substantially all of the phenolic impurities from the products stream and is fed by line 23 to a first wash tower 24 where the xylene filtrate is contacted with an aqueous NaOH stream 25. The aqueous NaOH stream reacts with and removes the phenolic impurities from the xylene filtrate to produce an aqueous phenolic impurity-containing waste caustic stream and a substantially phenolic impurity-free xylene-rich organic stream.

The xylene-rich organic stream is fed by line 26 to a second wash tower 27 where the organic stream is washed with water 33 to remove to any phenate salts and residual caustic and optionally to remove residual dissolved or entrained water in the xylene-rich organic stream. The resultant xylene-depleted stream that is free of phenolic impurities, caustic, and water is removed from the second wash tower 27 and recovered via line 28. Water wash effluent 34 containing trace caustic, phenate salts, and trace xylenes is typically routed to waste water treatment and could be combined with waste stream 18 and 29.

The aqueous phenolic impurity-containing waste caustic stream is removed from the wash tower 24 and in an advantageous embodiment recycled via line 29 to combine with and neutralize the acidic waste water stream removed from the multistage separator 14 via line 18. Part of the acidic waste water stream removed from the separator 14 can be recycled via line 32 to the reactor 12 to act as diluents in toluene methylation reaction.

Figure 2:
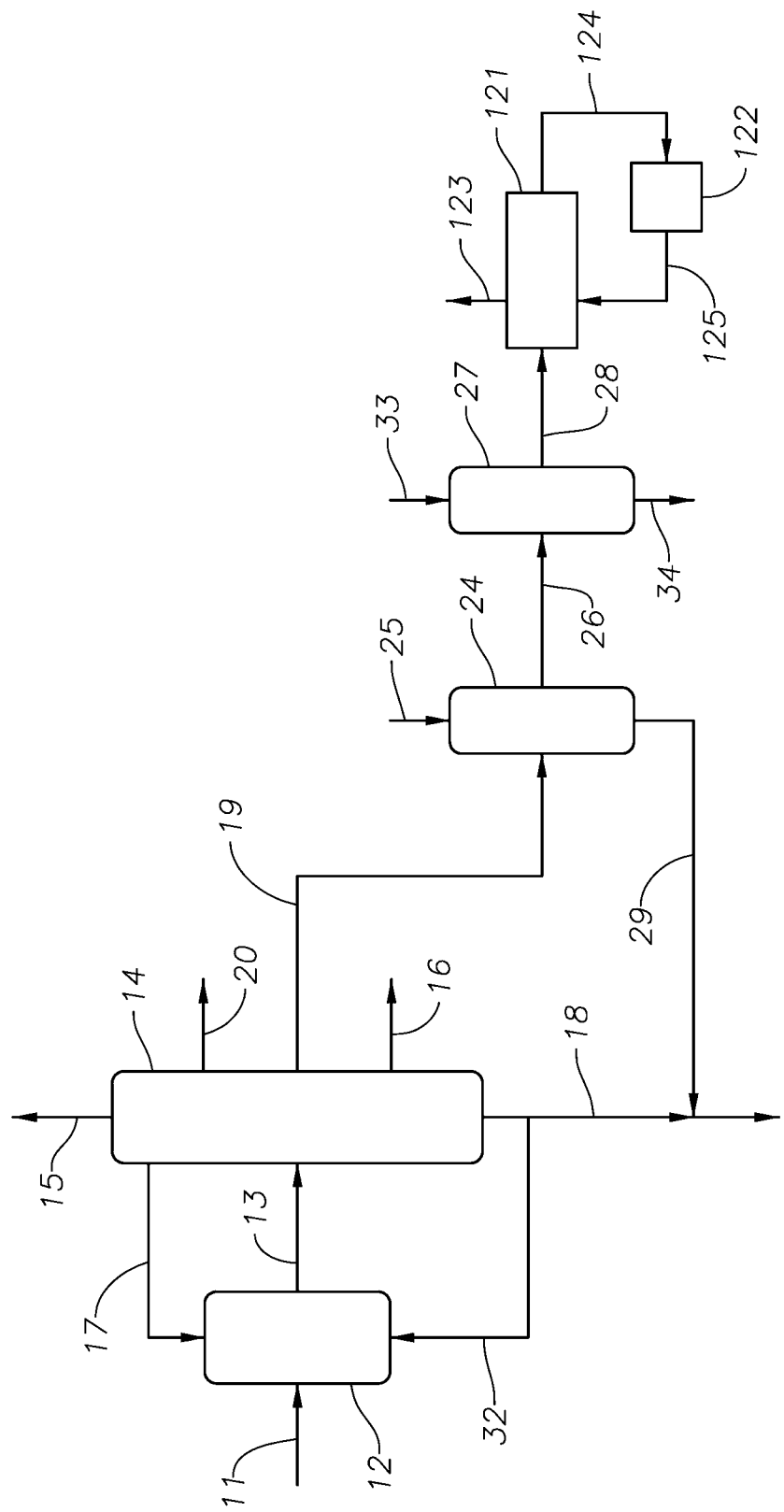

FIG. 2 illustrates another embodiment of the invention, wherein the caustic wash is upstream of a xylenes recovery system, such as a crystallizer (such as described above) or adsorption unit, the latter being exemplified by a Parex™ or Eluxyl™ Unit. FIG. 2 is the same as FIG. 1 with respect to alkylation unit 12, multistage separation unit 14, and conduits 11, 13, 15, 16, 17, 18, 20, and 32. However, in the embodiment shown schematically in FIG. 2, the product stream 19 comprising paraxylene is fed to caustic wash apparatus 24 and second wash tower 27 prior to paraxylene extraction in unit 121, which may be separation by, for instance, a Parex™ Unit, Eluxyl™ Unit, crystallizer, membrane, extraction, and the like, each per se known in the art. Input conduits 25 (caustic, such as NaOH) and 33 (water) and output conduits 29 (recycle of acidic waste caustic stream to combine with and neutralize the acidic waste water stream from multistage separator 14) and 34 are the same as in FIG. 1. The conduit 26 remains the output of wash 24 but has not yet been enriched in paraxylene when compared with the output 19 from the multistage separation system 14.

Continuing with the description of the embodiment described schematically in FIG. 2, the high purity xylene stream 28 from the caustic wash system, provided by units 24 and 27, is then sent to a paraxylene separation system provided by extraction unit 121, described above, yielding a paraxylene rich product stream 123 and a paraxylene-depleted raffinate 124 which can be sent to xylene isomerization unit 122, resulting in a equilibrium (e.g., 22-24 wt % paraxylene) xylenes stream 125, which may be sent back to paraxylene extraction unit 121. The "xylenes loop" described by unit 121, conduit 124, unit 122, and conduit 125 is per se well-known in the art. See, for instance, U.S. Publication 20110319688. The isomerization unit 122 may be a liquid isomerization unit or vapor-phase isomerization unit, both per se known in the art. The xylenes loop may be multi-unit, such as having multiple extraction units 121 and/or multiple isomerization units 122.

Figure 3:
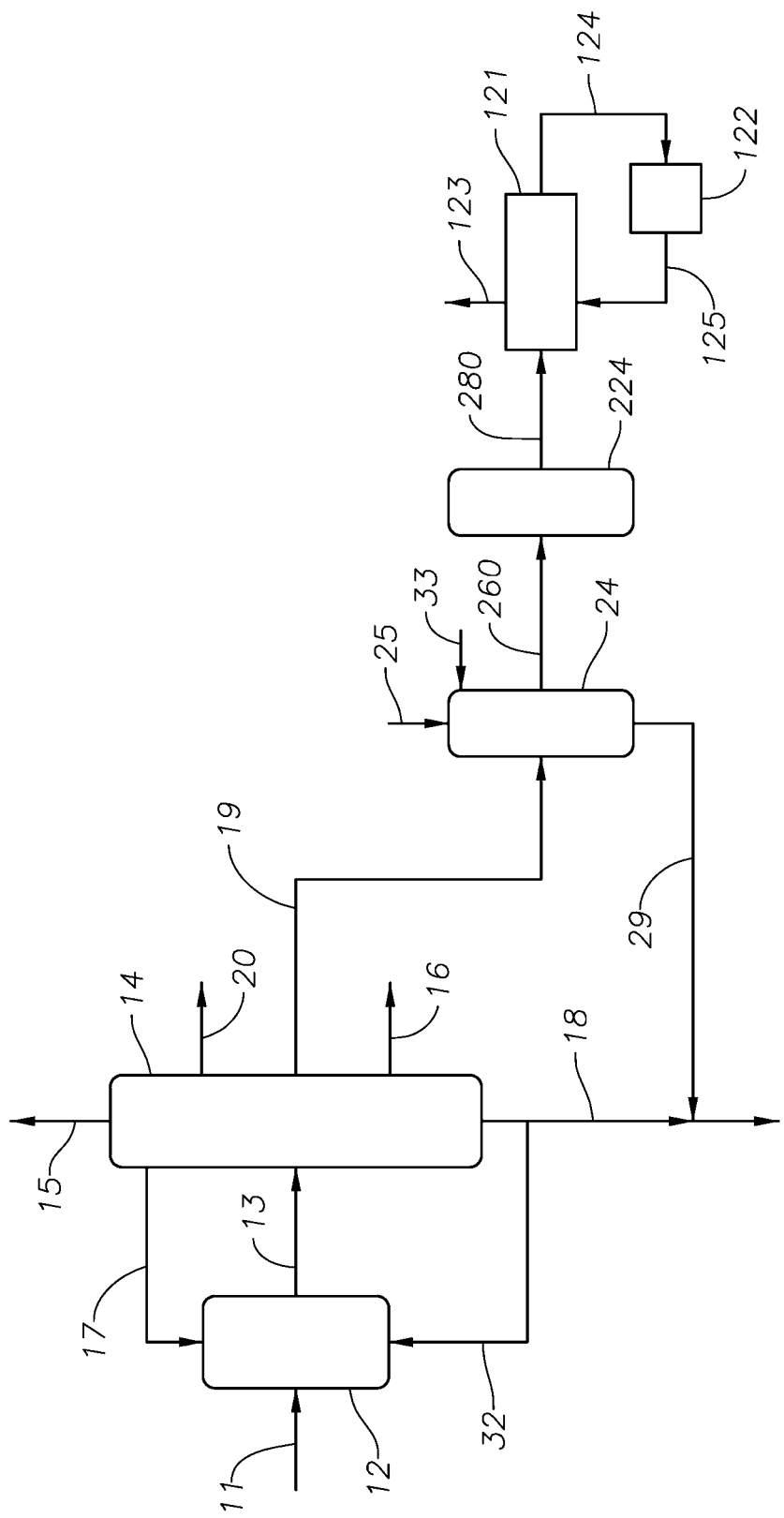

Another embodiment of the invention is described schematically in FIG. 3. FIG. 3 is similar to FIGS. 1 and 2 with respect to alkylation unit 12, multistage separation unit 14, and conduits 11, 13, 15, 16, 17, 18, 20, and 32. It is similar to FIG. 2 in that the paraxylene stream 19 from multistage separation unit 14 is first fed to a caustic wash system described by units 24 (with recycle of acidic waste caustic stream to combine with and neutralize the acidic waste water stream from multistage separator 14), and 224, prior to paraxylene separation unit 123. Unit 24 in FIG. 3 is a combination of two units shown in FIG. 2, that is, caustic wash unit 24 and the phenate salt removal step from unit 27. Unit 224 as depicted here is a trace caustic removal and optionally a subsequent drying step, which may, in an embodiment, utilize and ion exchange resin and/or a molecular sieve. Suitable resins have been discussed above. Appropriate molecular sieves are, by way of non-limiting example, 4A or 5A-type molecular sieves. Drying may also be accomplished by pasteurization.

Continuing with the description of the embodiment described schematically in FIG. 3, the high purity xylene stream 280 from the caustic wash system, provided by units 24 and 224, with is then sent to a paraxylene separation system, exactly as described with respect to FIG. 2, provided by extraction unit 121, described previously, yielding a paraxylene-rich product stream 123 and a paraxylene-depleted raffinate 124 which can be sent to xylene isomerization unit 122, resulting in a equilibrium xylenes stream 125, which may be sent back to paraxylene extraction unit 121, as in FIG. 2.

Figure 4:
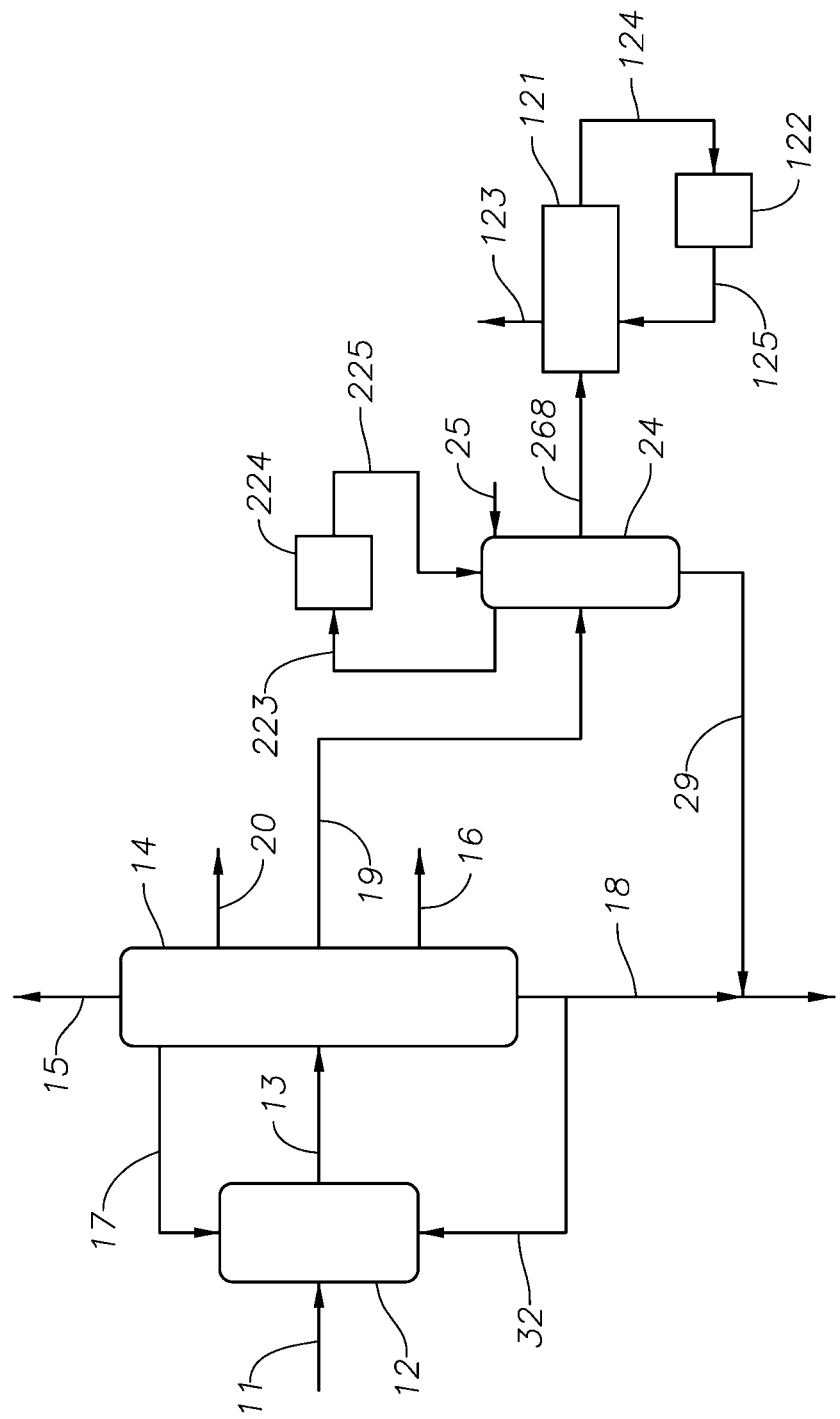

FIG. 4 is similar to FIG. 3 with respect to both upstream and downstream of caustic wash unit 24, and thus units 12, 14, 121, and 122 are identical to those in FIG. 3, as are associated conduits. However, in operation the caustic wash unit 24, provided with caustic 25, and recycle of aqueous phenolic impurity-containing waste caustic stream 29 as in the previous embodiments described in FIGS. 1-3, above. Trace caustic removal unit 224 is provided as a loop, wherein a recycled water stream 223 is contacted with unit 224 to remove trace caustic, such as by membrane, molecular sieve, water washing, and the like; this is within the skill of one of ordinary skill in the art in possession of this disclosure. Removal of trace caustic, among other things, reduces water consumption and reduces or eliminates waste water stream 29. The thus-purified water 225 is returned to the caustic wash system 24. The high purity xylenes stream from the caustic wash system 24 is then passed via conduit 268 to the paraxylene separation system described previously with respect to units 121 and 122 and associated conduits 124 and 125, to provide high purity, concentrated paraxylene product 123.

Figure 5:
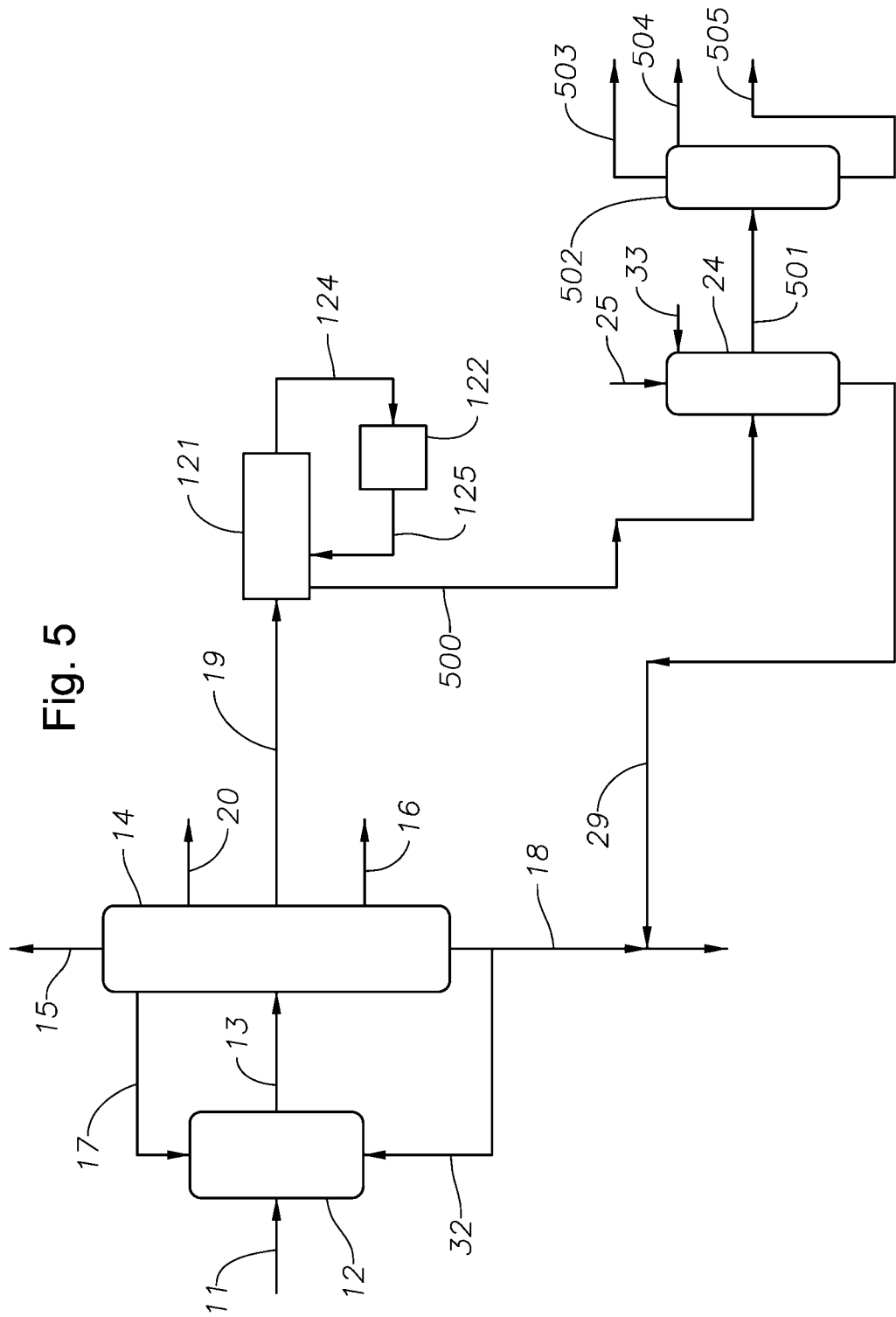

FIG. 5 illustrates an embodiment of the invention with a paraxylene removal stage prior to caustic wash. As in previous figures, alkylation unit 12, multistage separation unit 14, and conduits 11, 13, 15, 16, 17, 18, 20, and 32, are the same as previously described. Likewise, the paraxylene separation stage, described by the loop connecting the paraxylene separation unit 121 and the xylene isomerization unit 122, connected by conduits 124 and 125, is the same as previously described, except now this stage is directly connected via conduit 19 to separation unit 14. The highly concentrated paraxylene product of the paraxylene separation stage is sent via conduit 500 to caustic wash unit 24. In the embodiment shown schematically in FIG. 5, caustic wash unit 24 includes inputs of caustic 33 and water 25, and outputs including the recycle 29 of caustic waste and then passage of the concentrated, highly pure paraxylene to separation system 502 to remove water 503, product paraxylene 505 (free of phenols, caustic and water), and any other impurities such as toluene 504.

Figure 6:
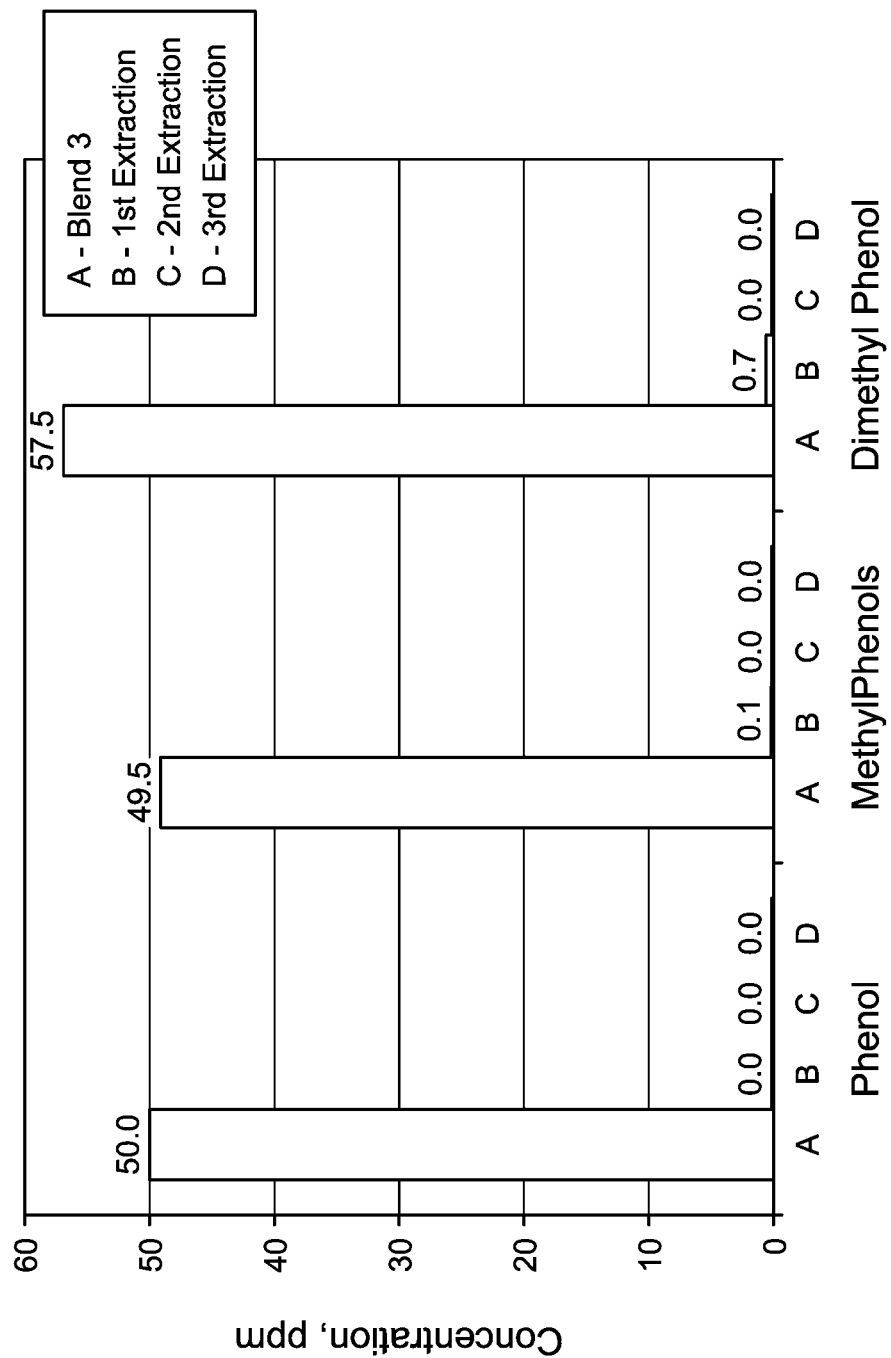
FIG. 6 is a graph showing the concentration of phenol, methyl phenols and dimethyl phenols in a xylene blend containing 50 ppmw each of phenol, methyl phenols and dimethyl phenols before and after first, second and third extractions with 1N NaOH solution according to Example 1.
Figure 7:
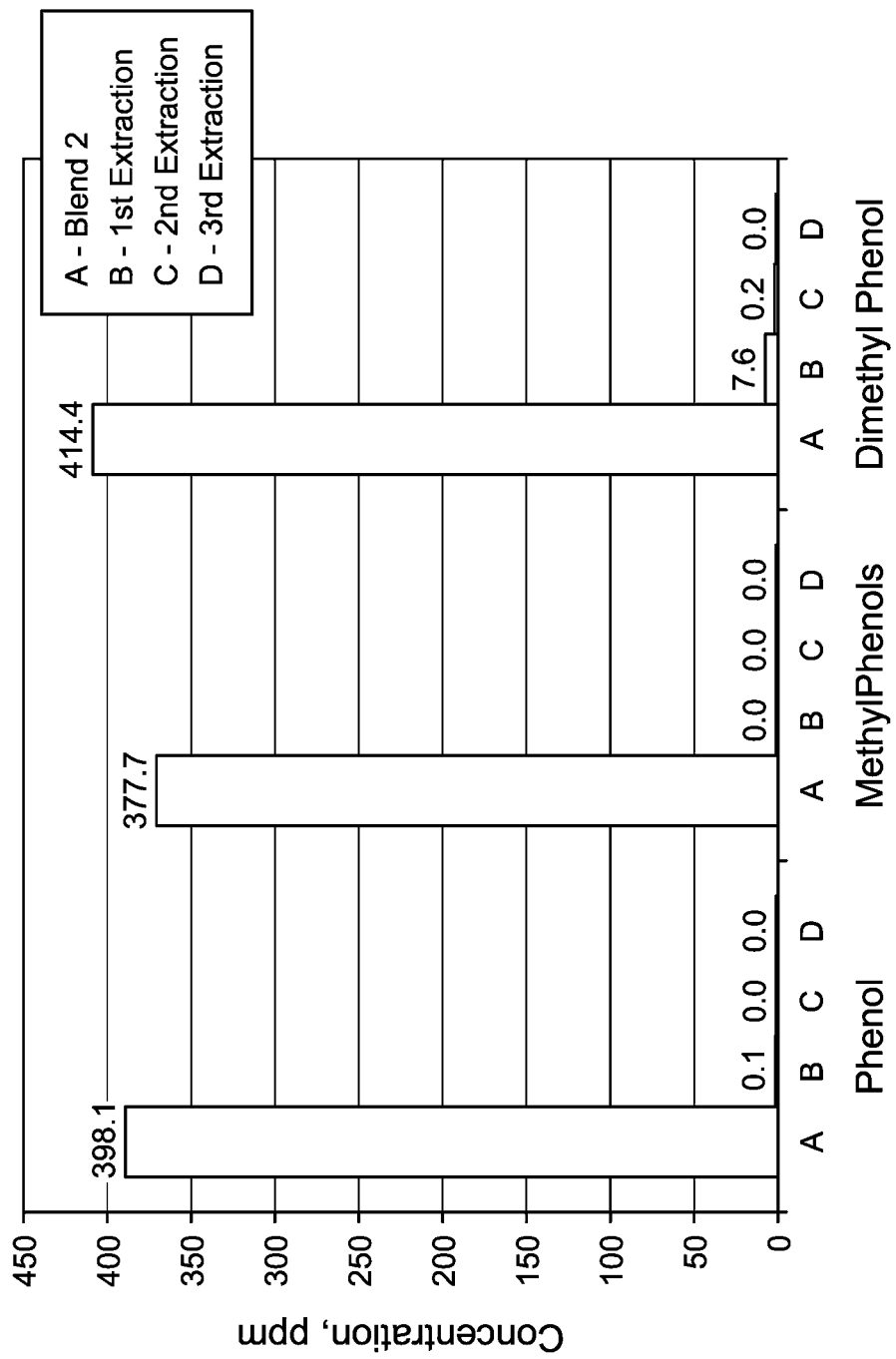
FIG. 7 is a graph showing the concentration of phenol, methyl phenols and dimethyl phenols in a xylene blend containing 500 ppmw each of phenol, methyl phenols and dimethyl phenols before and after first, second and third extractions with 1N NaOH solution according to Example 2.
Figure 8:
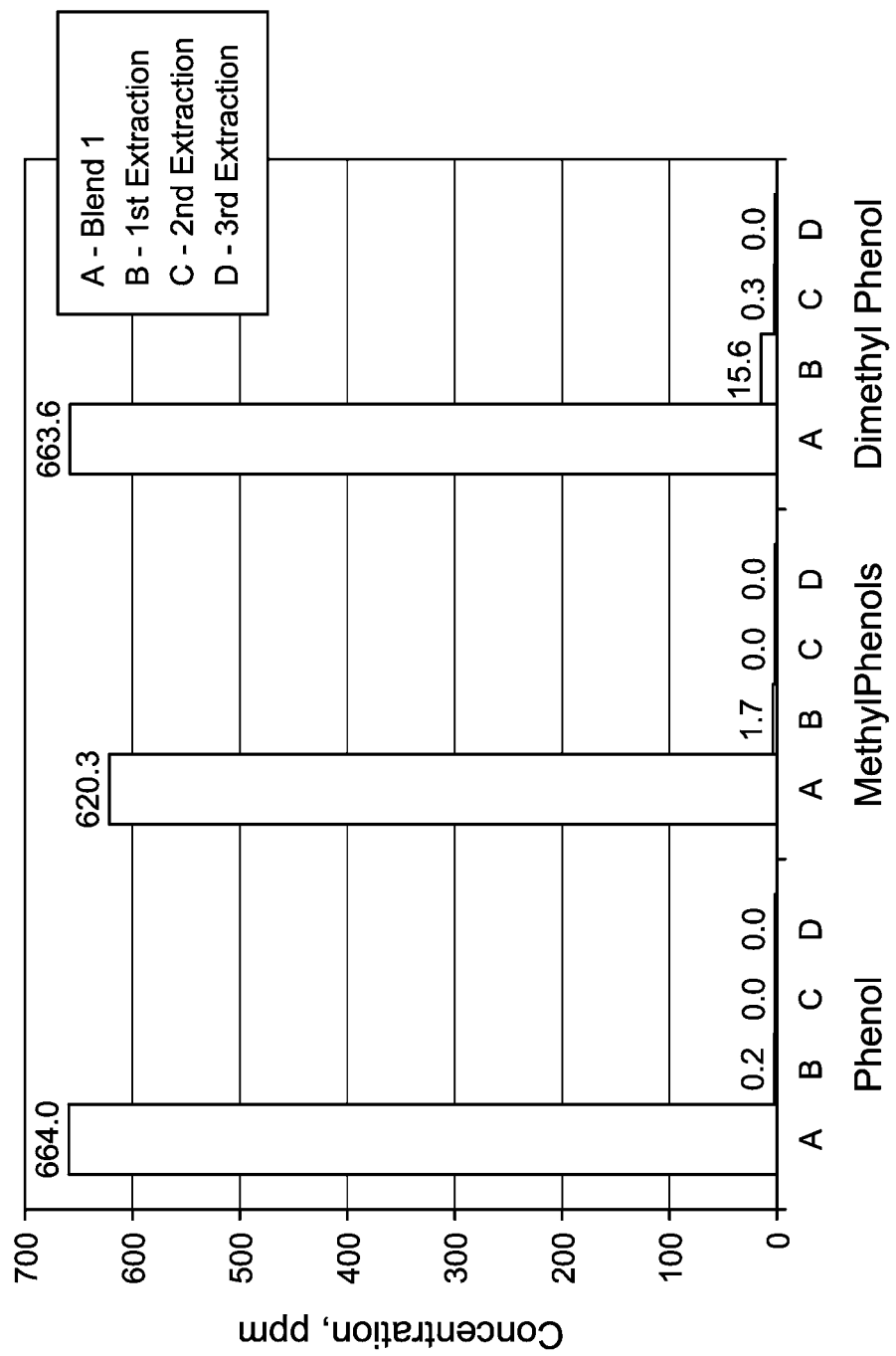
FIG. 8 is a graph showing the concentration of phenol, methyl phenols and dimethyl phenols in a xylene blend containing 1000 ppmw each of phenol, methyl phenols and dimethyl phenols before and after first, second and third extractions with 1N NaOH solution according to Example 3.

The invention will now be more particularly described with reference to the following non-limiting Examples, and FIGS. 6 to 8 of the accompanying drawings.

Example 1

A xylene blend containing 20 ml of nominal 50 ppmw phenol, 50 ppmw methyl phenols, and 50 ppmw dimethyl phenols respectively was prepared in a test tube. During a first extraction, 20 ml of 1N aqueous NaOH solution was added to the test tube, the test tube was capped and then shaken vigorously for 2 minutes. After the blend had stood for 10 minutes, the organic phase was sampled and analyzed for phenolic impurity concentrations. As shown in FIG. 6, the first extraction completely removed phenol, while leaving 0.1 ppm methyl phenols and 0.7 ppm of dimethyl phenols. After removing the aqueous phase from the test tube, the blend was extracted with 20 ml of the 1N NaOH solution for a second time. Following the same procedure as the first extract, the organic phase was sampled and analyzed for phenolic impurity concentrations. As shown in FIG. 6, the second NaOH extraction completely removed all phenolic impurities. A third NaOH extraction was conducted in the same way as the first and second extractions and confirmed that there was no phenolic impurities left after this extraction.

Example 2

A xylene blend containing 20 ml of nominal 500 ppmw phenol, 500 ppmw methyl phenols, and 500 ppmw dimethyl phenols respectively was prepared in a test tube. During a first extraction, 20 ml of 1N aqueous NaOH solution was added to the test tube, the test tube was capped and shaken vigorously for 2 minutes. After the blend stood for 10 minutes, the organic phase was sampled and analyzed for phenolic impurity concentrations. As shown in FIG. 7, the first extraction was able to remove most of the phenolic impurities while leaving only 0.1 ppmw of phenol, 0.8 ppmw of methyl phenols, and 7.6 ppm of dimethyl phenols. After removing aqueous phase from the test tube, the blend was extracted with 20 ml of the 1N NaOH solution for a second time. Following the same procedure as the first extract, the organic phase was sampled and analyzed for phenolic impurity concentrations. As shown in FIG. 7, the second NaOH extraction completely removed phenol and methyl phenol, and left only 0.2 ppm dimethyl phenols. A third NaOH extraction was conducted in the same way as the first and second extractions and all phenolic impurities were completely removed after this extraction.

Example 3

A xylene blend containing 20 ml of nominal 1000 ppmw phenol, 1000 ppmw methyl phenols, and 1000 ppmw dimethyl phenols respectively was prepared in a test tube. During a first extraction, 20 ml of 1N aqueous NaOH solution was added to the test tube, then the test tube was capped and shaken vigorously for 2 minutes. After the blend stood for 10 minutes, the organic phase was sampled and analyzed for phenolic impurity concentrations. As shown in FIG. 8, the first extraction was able to remove most of the phenolic impurities while leaving only 0.2 ppmw of phenol, 1.7 ppmw of methyl phenols, and 15.6 ppm of dimethyl phenols. After removing aqueous phase from the test tube, the blend was extracted with 20 ml of the 1N NaOH solution for a second time. Following the same procedure as the first extract, the organic phase was sampled and analyzed for phenolic impurity concentrations. As shown in FIG. 8 the second NaOH extraction completely removed phenol and methyl phenol, and left only 0.3 ppm dimethyl phenols. A third NaOH extraction was conducted in the same way as the first and second extractions and all phenolic impurities were completely removed after this extraction.

The present invention may be advantageously integrated with other systems that use toluene streams in a refinery and/or chemical plant, such as disproportionation processes and/or transalkylation processes.

While the present invention has been described and illustrated by reference to particular embodiments, those of ordinary skill in the art will appreciate that the invention lends itself to variations other than those specifically illustrated herein.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

The invention claimed is:

1. A process for producing paraxylene, the process comprising:
   (a) alkylating benzene and/or toluene with methanol in the presence of a catalyst under conditions effective to convert said benzene and/or toluene to xylene and produce a product stream containing water, xylene and one or more phenolic impurities, wherein said catalyst comprises a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa), wherein said porous crystalline material has undergone prior treatment with steam at a temperature of at least 950° C. for between about 10 minutes and about 100 hours to adjust the Diffusion Parameter of said material to about 0.1-15 $sec^{-1}$;
   (b) separating said product stream into a water-rich stream and a xylene-rich stream containing one or more phenolic impurities; and
   (c) contacting at least a portion of said xylene-rich stream with an aqueous solution of a base in a plurality of stages under conditions to reduce the level of phenolic impurities in said xylene-rich stream to less than 0.1 ppmw, wherein said xylene-rich stream is in a liquid phase; then
   (d) washing said xylene-rich stream with water to remove any phenate salts and any residual aqueous solution of base; then
   (e) a step of separation of paraxylene from said xylene-rich stream by adsorptive separation to leave a paraxylene-depleted stream.

2. The process of claim 1, wherein the phenolic impurities are selected from phenol, methyl phenol and dimethyl phenol.

3. The process of claim 2, wherein the xylene-rich stream portion contacted with said aqueous solution of a base in (c) comprises phenolic impurities in an amount up to about 1000 ppmw.

4. The process of claim 1, wherein the base comprises an alkali metal compound.

5. The process of claim 1, wherein the base is sodium hydroxide.

6. The process of claim 1, wherein said aqueous solution comprises a 0.01 N to 10 N sodium hydroxide solution.

7. The process of claim 1, wherein said contacting (c) is conducted for a time from about 0.5 to about 60 minutes.

8. The process of claim 1, further comprising:
   (f) recovering said water after said washing (d) as a recycle water stream;

(g) purifying said recycle water stream to remove said phenate salts and residual aqueous solution of base to produce a purified water stream; and
(h) introducing said purified water stream as said water in said washing (d).

9. The process of claim 1, further comprising isomerizing said paraxylene-depleted steam in a xylene isomerization unit.

10. The process of claim 1, further comprising transalkylating said paraxylene-depleted stream in a transalkylation unit.

* * * * *